(12) United States Patent
Perricaudet et al.

(10) Patent No.: US 6,669,942 B2
(45) Date of Patent: *Dec. 30, 2003

(54) DEFECTIVE ADENOVIRUSES INCLUDING A THERAPEUTIC GENE AND AN IMMUNOPROTECTOVE GENE

(75) Inventors: Michel Perricaudet, Ecrosnes (FR); Martin Lee, Paris (FR)

(73) Assignee: Aventis Pharma S.A., Antony Cedex (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/817,494

(22) PCT Filed: Oct. 11, 1995

(86) PCT No.: PCT/FR95/01326

§ 371 (c)(1),
(2), (4) Date: Apr. 15, 1997

(87) PCT Pub. No.: WO96/12030

PCT Pub. Date: Apr. 25, 1996

(65) Prior Publication Data

US 2002/0006395 A1 Jan. 17, 2002

(30) Foreign Application Priority Data

Oct. 17, 1994 (FR) .............................. 94 12346

(51) Int. Cl.[7] .............................. A61K 39/12
(52) U.S. Cl. ............... 424/199.1; 424/233.1; 435/320.1; 435/69.1; 536/23.72
(58) Field of Search ............. 514/44; 424/233.1, 424/93.21, 199.1; 435/320.1, 69.1; 536/23.72

(56) References Cited

FOREIGN PATENT DOCUMENTS

| WO | WO 93/06867 | 4/1993 |
|---|---|---|
| WO | WO 93/19191 | 9/1993 |
| WO | WO 94/04196 | 3/1994 |
| WO | 94/12649 A * | 6/1994 |
| WO | WO 94/28152 | 12/1994 |

OTHER PUBLICATIONS

Haddada et al, 1993, Human Gene Theraphy, vol. 4, pp. 703–711.*
Rawle et al, 1989, The Journal of Immunology, vol. 143, pp. 2031–2037.*
Burgert et al, 1987, PNAS USA, vol. 84, pp. 1356–1360.*
Gooding et al, 1988, Cell, vol. 53, pp. 341–346.*
Marshall, 1995, Science, vol. 269, pp. 1050–1055.*
Orkin et al, 1995, NIH Panel Report on Gene Theraphy.*
Kafri et al . PNAS, Sep. 1998, vol. 95, pp. 11377–11382.*
Bett et al . PNAS, Sep. 1994, vol. 91, pp, 8802–8806.*
Ranheim et al., Characterization of Mutants within the Gene for the Adenovirus E3 14.7–Kilodalton Protein Which Prevents Cytolysis by Tumor Necrosis Factor, J. of Virology, 67(4) p. 2159–2167 (1993).
Kremer et al., Adenovirus and adeno–associated virus mediated gene transfer, British Medical Bulletin 51(1), p. 31–44, (1995).
Lee et al., The constitutive expression of the immunomodulatory gp 19k protein in E1–, E3– adenoviral vectors strongly reduces the host cytotoxic T cell response against the vector, Gene Therapy 2, p. 256–262, (1995).

* cited by examiner

*Primary Examiner*—Ali R. Salimi
(74) *Attorney, Agent, or Firm*—Wiley Rein & Fielding LLP (57) ABSTRACT

Novel adenovirus-derived viral vectors, the preparation thereof, and the use of such vectors in gene therapy, are disclosed. In particular, defective adenoviruses having a genome that includes a first recombinant DNA containing a therapeutic gene and a second recombinant DNA containing an immunoprotective gene, are disclosed.

28 Claims, 4 Drawing Sheets

DEFECTIVE ADENOVIRUSES INCLUDING A THERAPEUTIC GENE AND AN IMMUNOPROTECTOVE GENE

This application is a 371 of International Application PCT/FR95/01326, filed Oct. 11, 1995, and which designated the United States.

The present invention relates to new viral vectors, to their preparation and to their use in gene therapy. It also relates to pharmaceutical compositions containing the said viral vectors. More especially, the present invention relates to recombinant adenoviruses as vectors for gene therapy.

Gene therapy consists in correcting a deficiency or an abnormality (mutation, aberrant expression, and the like) by introducing genetic information into the cell or organ affected. This genetic information may be introduced either in vitro into a cell extracted from the organ, the modified cell then being reintroduced into the body, or directly in vivo into the appropriate tissue. In this second case, different techniques exist, including various techniques of transfection involving complexes of DNA and DEAE-dextran (Pagano et al., J.Virol. 1 (1967) 891), of DNA and nuclear proteins (Kaneda et al., Science 243 (1989) 375) and of DNA and lipids (Felgner et al., PNAS 84 (1987) 7413), the use of liposomes (Fraley et al., J.Biol.Chem. 255 (1980) 10431), and the like. More recently, the use of viruses as vectors for gene transfer has been seen to be a promising alternative to these physical transfection techniques. In this connection, different viruses have been tested for their capacity to infect certain cell populations. This applies especially to retroviruses (RSV, HMS, MMS, and the like), the HSV virus, adeno-associated viruses and adenoviruses.

Figure 1:
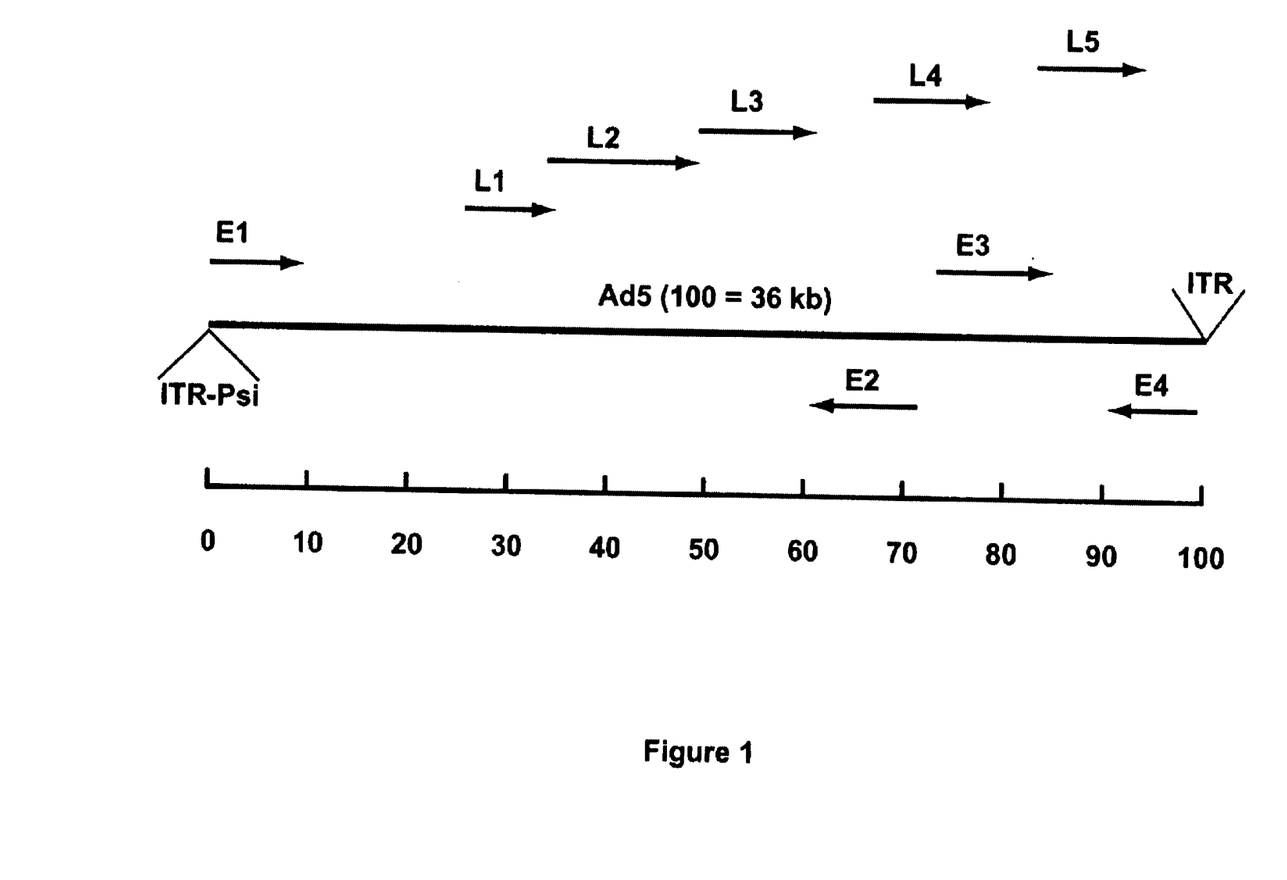
Figure 2:
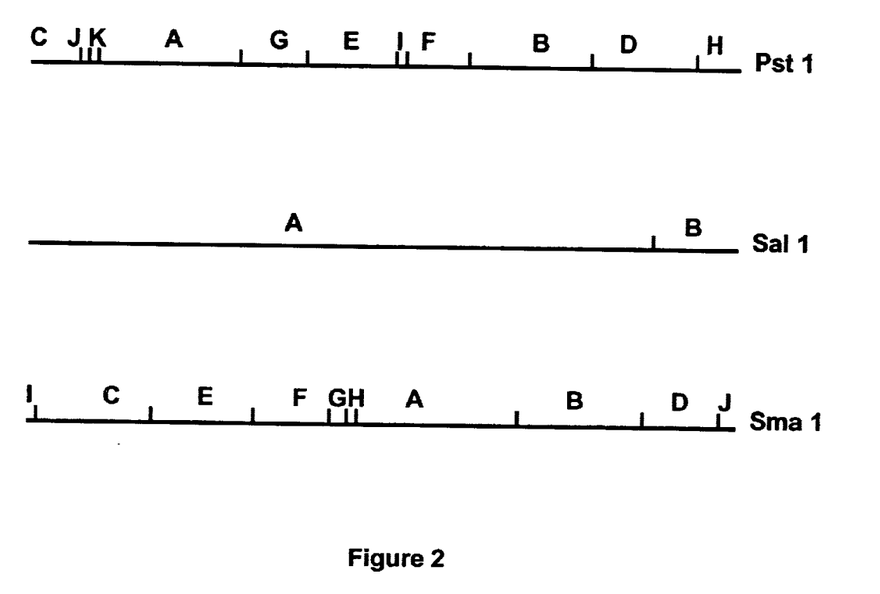
FIG. 2: Restriction map of the CAV2 adenovirus strain Manhattan (from Spibey et al., cited above).

Among these viruses, the adenoviruses display certain properties which are advantageous for use in gene therapy. In particular, they have a fairly broad host range, are capable of infecting resting cells and do not integrate in the genome of the infected cell. Adenoviruses are linear, double-stranded DNA viruses approximately 36 kb in size. Their genome comprises, in particular, an inverted repeat sequence (ITR) at their end, an encapsidation sequence, early genes and late genes (see FIG. 1). The main early genes are the E1 (E1a and E1b), E2, E3 and E4 genes. The main late genes are the L1 to L5 genes.

In view of the properties of adenoviruses, mentioned above, the latter have already been used for in vivo gene transfer. To this end, different vectors derived from adenoviruses have been prepared, incorporating different genes (β-gal, OTC, α-1AT, cytokines, and the like). In each of these constructions the adenovirus has been modified so as to render it incapable of replication in the infected cell. Thus, the constructions described in the prior art are adenoviruses from which the E1 (E1a and/or E1b) and, where appropriate, E3 regions have been deleted, in which regions a heterologous DNA sequence is inserted(Levrero et al., Gene 101 (1991) 195; Gosh-Choudhury et al., Gene 50 (1986) 161).

However, as in the case of all known viruses, the administration of a wild-type adenovirus induces a substantial immune response (Routes et al., J. Virol 65 (1991) 1450). This immunogenicity has also been observed following the administration of recombinant adenoviruses which are defective for replication (Yang et al., PNAS (1994) 4407). One of the major roles of the immune system consists, in effect, in destroying non-self or altered-self elements. The administration of a gene therapy factor of adenoviral origin introduces non-self units into the body. Similarly, cells infected with such a vector and expressing, as a result, an exogenous therapeutic gene become altered-self elements. Hence it is normal for the immune system to react against these vectors and infected cells as if they were foreign bodies. This immune response to infected cells constitutes a major obstacle to the development of these viral vectors, since (i) by inducing a destruction of the infected cells, it limits the period of expression of the therapeutic gene and hence the therapeutic effect, (ii) it induces a substantial concomitant inflammatory response, and (iii) it brings about rapid elimination of the infected cells after repeated injections. Thus, the expression of β-galactosidase encoded by a recombinant adenovirus administered in the muscle of immunocompetent mice is reduced to minimum levels 40 days after injection (Kass-Eisler et al., PNAS 90 (1993) 11498). Similarly, the expression of gene transferred by adenoviruses into the liver is significantly reduced after 4 months (Li et al., Hum. Gene Ther. 4 (1993) 403), and the expression of factor IX transferred by adenoviruses into hepatocytes of haemophilic dogs disappears 100 days after injection (Kay et al., PNAS 91 (1994) 2353).

Hence it would appear that the exploitation of vectors derived from adenoviruses in gene therapy entails the possibility of reducing the immune response to these vectors or the infected cells. This constitutes specifically the subject of the present invention. The present invention relates, in effect, to new vectors derived from adenoviruses displaying an immunogenicity which is greatly reduced or even eliminated. The vectors of the invention are hence especially suitable for gene therapy applications, in particular in man.

A first subject of the present invention relates to a defective adenovirus whose genome comprises a first recombinant DNA containing a therapeutic gene and a second recombinant DNA containing an immunoprotective gene.

The present invention is partly the outcome of the demonstration that it is possible to incorporate several genes of interest in adenoviruses, and to obtain a substantial expression of these different genes in the infected cells. The present invention is also the outcome of the construction of adenoviral vectors capable of incorporating several therapeutic genes under conditions permitting their optimal expression. It is also the outcome of the demonstration that coexpression in the infected cell of certain genes is capable of inducing an immunoprotective effect, and thus of leading the vectors of the invention and/or the infected cells to evade the immune system. The present invention thus provides viral vectors displaying immunological and therapeutic properties which are thoroughly advantageous for the purpose of their use in gene or cell therapy.

The recombinant DNAs according to the present invention are DNA fragments containing the gene in question (therapeutic or immunoprotective) and optionally signals permitting its expression, constructed in vitro and then inserted into the adenovirus genome. The recombinant DNAs used in the context of the present invention can be complimentary DNAs (cDNA), genomic DNAs (gDNA) or hybrid constructions consisting, for example, of a cDNA into which one or more introns might be inserted. They can also be synthetic or semi-synthetic sequences. These DNAs may be of human, animal, vegetable, bacterial, viral, and the like, origin. It is especially advantageous for cDNAs or gDNAs to be used.

The insertion of the genes in question in the form of recombinant DNAs according to the invention affords greater flexibility in the construction of the adenoviruses, and permits better control of the expression of the said genes.

Thus, the recombinant DNAs, (and hence the two genes of interest) incorporated in the adenoviral vectors according to the invention may be organized in different ways.

In the first place, they may be inserted at the same site of the adenovirus genome or at selected, different sites. In particular, the recombinant DNAs may be inserted at least partially in the E1, E3 and/or E4 regions of the adenovirus genome, replacing or in addition to viral sequences.

Next, they may each contain a transcription promoter, which may be identical or different. This configuration enables higher levels of expression to be obtained, and affords better control of the expression of the genes. In this case, the two genes may be inserted in the same orientation or in opposite orientations.

They may also constitute a single transcriptional entity. In this configuration the two recombinant DNAs are adjacent and positioned in such a way that both genes are under the control of a single promoter and give rise to a single premessenger RNA. This arrangement is advantageous since it enables a single transcription promoter to be used.

Lastly, the use of recombinant DNAs according to the invention enables transcription promoters of different natures to be used, and in particular strong or weak, regulated or constituted, tissue-specific or ubiquitous, and the like, promoters.

The choice of expression signals and of the respective position of the recombinant DNAs is especially important for obtaining a high expression of the therapeutic gene and a substantial immunoprotective effect.

As a therapeutic gene which may be used for the construction of the vectors of the present invention, any gene coding for a product having a therapeutic effect may be mentioned. The product thus encoded can be a protein, a peptide, an RNA, and the like.

In the case of a proteinaceous product, this can be homologous with respect to the target cell (that is to say a product which is normally expressed in the target cell when the latter does not display any pathology). In this case, the expression of a protein makes it possible, for example, to compensate for an insufficient expression in the cell or for the expression of a protein that is inactive or poorly active as a result of a modification, or alternatively to overexpress the said protein. The therapeutic gene can also code for a mutant of a cellular protein, having enhanced stability, modified activity, and the like. The proteinaceous product can also be heterologous with respect to the target cell. In this case, an expressed protein can, for example, supplement or supply an activity which is deficient in the cell, enabling it to combat a pathology, or stimulate an immune response.

Among proteinaceous products which are therapeutic for the purposes of the present invention, there may be mentioned, more especially, enzymes, blood derivatives, hormones, lymphokines, namely interleukins, interferons, TNF, and the like (FR 92/03120), growth factors, neurotransmitters or their precursors or synthetic enzymes, trophic factors, namely BDNF, CNTF, NGF, IGF, GMF, aFGF, bFGF, NT3, NTS, HARP/pleiotrophin, and the like; apolipoproteins, namely ApoAI, ApoAIV, ApoE, and the like (FR 93/05125), dystrophin or a minidystrophin (FR 91/11947), the CFTR protein associated with cystic fibrosis, tumour-suppressing genes, namely p53, Rb, RaplA, DCC, k-rev, and the like (FR 93/04745), genes coding for factors involved in coagulation, namely factors VII, VIII, IX, genes participating in DNA repair, and the like.

As mentioned above, the therapeutic gene can also be an antisense gene or sequence, the expression of which in the target cell enables the expression of cellular genes or the transcription of cellular mRNA to be controlled. Such sequences can, for example, be transcribed in the target cell into RNAs complementary to cellular mRNAs, and can thus block their translation into protein, according to the technique described in Patent EP 140,308. Antisense sequences also include sequences coding for ribozymes, which are capable of selectively destroying target RNAs EP 321,201).

As mentioned above, the therapeutic gene can also contain one or more genes coding for an antigenic peptide capable of generating an immune response in humans or animals. In this particular embodiment, the invention hence makes it possible to produce either vaccines or immunotherapeutic treatments applied to humans or to animals, in particular against microorganisms, viruses or cancers. Such antigenic peptides can be, in particular, specific to the Epstein-Barr virus, the HIV virus, the hepatitis B virus (EP 185,573) or the pseudorabies virus, or alternatively tumour-specific (EP 259,212). In this embodiment, no immune response will be generated against the vector virus or the infected cell, but the selected antigen will be produced and will alone be capable of being immunogenic.

The therapeutic genes may be of human, animal, vegetable, bacterial, viral, and the like, origin. They may be obtained by any technique known to a person skilled in the art, and in particular by the screening of libraries, by chemical synthesis or alternatively by mixed methods including chemical or enzymatic modification of sequences obtained by the screening of libraries.

The immunoprotective gene used in the context of the present invention can be of different types. More preferably, the Applicant has now shown that the use of a gene whose product affects the activity of the major histocompatibility complex (MHC) or affects cytokine activity makes it possible to reduce considerably, or even to eliminate, any immune reaction against the vector or the infected cells. The vectors thereby obtained are especially advantageous, since they possess much longer-lasting action in vivo and hence a greater therapeutic effect, lack an inflammatory and immunogenic effect and may be used with a reduced number of injections.

Antigen presenting cells present antigenic peptides at their surface, in combination with molecules of the major histocompatibility complex class I (MHC-I). The receptors of cytotoxic T cells (CTL) recognize the complexes formed between the said MHC class I molecules and the said antigenic peptides. This recognition induces cell death by CTL. The Applicant has now shown that it is possible to coexpress in an adenoviral vector a therapeutic gene and a gene capable of impairing the expression of MHC-I molecules, and that this coexpression produces a lasting therapeutic effect without immune or inflammatory reactions. Among genes whose product affects the activity of the major histocompatibility complex, it is preferable to use in the context of the invention genes whose product at least partially inhibits the expression of the MHC proteins or antigen presentation. As preferred examples, certain genes contained in the adenovirus E3 region, the herpes virus ICP47 gene or the cytomegalovirus UL18 gene may be mentioned.

The E3 region of the adenovirus genome contains different reading frames which, by alternative splicing, give rise to different proteins. Among the latter, the Gp19k (or E3–19k) protein is a glycosylated transmembrane protein localized in the membrane of the endoplasmic reticulum (ER). This protein comprises a luminal domain binding MHC-I molecules and a C-terminal cytoplasmic end capable of binding microtubules (or tubulin), which acts to anchor the gp19k protein in the membrane of the ER. Gp19k is thus capable of preventing the expression of the MHC-I molecules at the cell surface by interaction and sequestration in the ER. However, in the absence of viral replication, the gp19k protein is weakly expressed by adenoviruses. The native promoter contains, in effect, some regulatory elements, such as binding elements of the NF-kB type, which limit the conditions for expression of this protein. Moreover, the expression of gp19k is also dependent on the production of an alternative splicing. Introduction into the vectors of the invention of a recombinant DNA containing a sequence (preferably cDNA) coding for gp19k enables the expression of the said protein to be controlled and optimized. In particular, the use of constituted promoters and the elimination of the other reading frames makes it possible to increase greatly the expression of this protein and to escape from the dependence on viral replication and the presence of inducing elements. This makes it possible in an especially advantageous way to decrease considerably the lysis of the infected cells by CTL and thus to increase and prolong the in vivo production of the therapeutic gene. The examples in the present application describe, in particular, the construction of a defective adenovirus carrying a recombinant DNA comprising a marker gene under the control of the RSV promoter, and a second recombinant DNA carrying a sequence coding for the gp19k protein under the control of the RSV constitutive promoter (Ad-βgal-gp19k). The results presented demonstrate that cells infected with this vector express β-galactosidase at levels which are as high as cells infected with an adenovirus containing only the β-gal gene. This shows that the presence of the second recombinant DNA does not affect the levels of expression of the first one. Next, the results presented show that cells infected with the Ad-βgal-gp19k adenovirus are protected against lysis by CTL, which is not the case with cells infected with an Ad-βgal adenovirus. Furthermore, the presence of the second recombinant DNA in the vectors of the invention inhibits the clonal expansion of lymphocytes directed against the infected cells. The vectors of the invention hence induce a significant reduction in the immune response by the CTL to the infected cells.

Other proteins encoded by the E3 region of the adenovirus genome, such as the 10.4k and 14.5k proteins, display some properties which are advantageous for the purpose of their incorporation in the vectors of the invention.

The herpes simplex virus ICP47 gene constitutes another immunoprotective gene which is especially advantageous for the purposes of the present invention. Cells infected with the herpes simplex virus display a resistance to CTL-induced lysis. It has been shown that this resistance could be conferred by the ICP47 gene, which is capable of reducing the expression of the MHC-I molecules at the cell surface. Incorporation of the ICP47 gene in a recombinant DNA according to the invention also enables the recombinant viruses of the invention to evade the immune system.

The cytomegalovirus UL18 gene constitutes another preferred example of an immunoprotective gene according to the invention. The UL18 gene product is capable of binding $\beta_2$-microglobulin (Browne et al. Nature 347 (1990) 770). $\beta_2$-Microglobulin is one of the chains of MHC-I molecules. Incorporation of the UL18 gene in a recombinant DNA according to the invention thus makes it possible to decrease the number of functional $\beta_2$-microglobulin molecules in the cells infected with the viruses of the invention, and hence to decrease the capacities of these cells to produce complete and functional MHC-I molecules. This type of construction hence enables the infected cells to be protected from lysis by CTL.

As mentioned above, the immunoprotective gene used in the context of the present invention is, in another preferred embodiment, a gene whose product affects the activity or the pathways of signalling of cytokines. The cytokines constitute a family of secreted proteins which act as signalling molecules for the immune system. They can attract the cells involved in immunity, activate them, induce their proliferation and even act directly on the infected cells to kill them.

Among the genes whose product affects the activity or the pathways of signalling of cytokines, there may be mentioned the genes participating in the synthesis of cytokines, or whose product is capable of sequestering cytokines, of antagonizing their activity or of interfering with the intercellular signalling pathways. As preferred examples, special mention may be made of the Epstein-Barr virus BCRF1 gene, the cowpox virus crmA and crmB genes, the vaccinia virus B15R and B18R genes, the cytomegalovirus US28 gene and the adenovirus E3-14.7, E3-10.4 and E3-14.5 genes.

The vaccinia virus B15R gene codes for a soluble protein capable of binding interleukin-1β (the secreted form of interleukin-1), and thus of preventing this cytokine from binding to its cell receptors. Interleukin-1 is, in effect, one of the first cytokines produced in response to an antigen attack, and it plays a very important part in the signalling of the immune system at the beginning of infection. The possibility of incorporating the B15R gene in a vector according to the invention advantageously enables IL-1β activity to be reduced, in particular as regards the activation of immune cells, and as a result enables the cells infected with the viruses of the invention to be protected locally against a substantial immune response. Genes homologous with the B15R gene may also be used, such as the cowpox virus— gene.

In the same way, the vaccinia virus B18R gene codes for a protein homologous with the interleukin-6 receptor. This gene, or any functional homologue, may also be used in the vectors of the invention to inhibit the binding of interleukin-6 to its cell receptor and thus to reduce the immune response locally.

Still in the same way, the cowpox virus crmB gene may be advantageously used. This gene codes, in effect, for a secreted protein capable of binding TNF and of competing with the TNF receptors at the cell surface. Hence this gene makes it possible, in the viruses of the invention, to decrease locally the concentration of active TNF capable of destroying the infected cells. Other genes coding for proteins capable of binding TNF and of at least partially inhibiting its binding to its receptors may also be used.

The cowpox virus crmA gene, for its part, codes for a protein having a protease inhibitor activity of the spermine type, which is capable of inhibiting the synthesis of interleukin-1. This gene may hence be used to decrease the concentration of interleukin-1 locally and thus to reduce the development of the immune and inflammatory response.

The Epstein-Barr virus BCRF1 gene codes for an analogue of interleukin-10. The product of this gene is a cytokine capable of decreasing the immune response and of changing its specificity while inducing the proliferation of B lymphocytes.

The cytomegalovirus US28 gene codes for a protein homologous with the receptor for macrophage inflammatory protein 1α (MIP-1α). This protein is hence capable of acting as a competitor for the MIP receptors, and hence of inhibiting its activity locally.

The product of the adenovirus E3-14.7, E3-10.4 and E3-14.5 genes is capable of blocking the transmission of the intercellular signal mediated by certain cytokines. When the cytokines bind to their receptor at the surface of an infected cell, a signal is transmitted to the nucleus to induce cell death or stop protein synthesis. This is especially the case with tumour necrosis factor (TNF). Incorporation of the E3-14.7, E3-10.4 and/or E3-14.5 genes in a recombinant DNA according to the invention for the purpose of their constitutive or regulated expression enables TNF-induced intercellular signalling to be blocked, and thus enables the cells infected with recombinant viruses of the invention to be protected from the toxic effects of this cytokine.

A local and transient inhibition may be especially advantageous. It may be obtained, in particular, by the choice of the particular expression signals (cytokine-dependent promoters for example), as described below.

It should be understood that other homologous genes or genes having similar functional properties may be used for the construction of the vectors of the invention. These different genes may be obtained by any technique known to a person skilled in the art, and in particular by the screening of libraries, by chemical synthesis or alternatively by mixed methods including the chemical or enzymatic modification of sequences obtained by the screening of libraries. In addition, these different genes may be used alone or in combination(s).

One of the other important aspects of the present invention relates to the choice of transcription promoters used for directing the expression of the genes. As mentioned above, it may be especially important to use a promoter capable of constitutively expressing the gene placed under its control. This is the case, for example, with the gp19k gene or a homologue, if it is desired to obtain substantial immunoprotection. In contrast, to control the expression of an immunoprotective gene affecting cytokine activity, a regulated expression may be desirable. As regards the expression of the therapeutic gene, the choice of expression signals depends on the nature of the therapeutic product, the pathology in question and the tissue targeted.

The promoters which may be used for the construction of the recombinant DNAs of the invention can be the promoters which are naturally responsible for the expression of the therapeutic or immunoprotective gene in question when they are capable of functioning in the infected cell. However, they are preferably sequences of different origin (responsible for the expression of other proteins, or even synthetic), especially for controlling the expression of the immunoprotective gene. In particular, they can be promoter sequences of eukaryotic or viral genes. For example, they can be promoter sequences originating from the genome of the cell which it is desired to infect. Similarly, they can be promoter sequences originating from the genome of a virus, including the adenovirus used. In this connection, the promoters of the E1A, MLP, CMV, RSV, and the like, genes may be mentioned for example. In addition, these expression sequences may be modified by the addition of activator or regulatory sequences or sequences permitting a tissue-specific expression. Moreover, when the recombinant DNA does not contain expression sequences, it may be inserted into the genome of the defective virus downstream of such a sequence. A preferred promoter for the production of the vectors of the invention consists of the Rous sarcoma virus LTR (RSVLTR). Since this promoter is constitutive and strong, it enables substantial immunoprotection to be induced by gp19k. Mammalian promoters may also be of great interest, such as the promoter of the PGK, albumin, and the like, genes. It can be especially advantageous to use regulated or tissue-specific promoters so as to be able to target the synthesis of the therapeutic and/or immunoprotective products. In particular, for the expression of an immunoprotective gene inhibiting cytokine activity, it can be especially advantageous to use an inducible promoter in order to obtain a localized effect. Inducible promoters are, for example, cytokine-induced promoters, so that the immunoprotective effect takes place only in response to an immune reaction.

Moreover, the recombinant DNA can also contain a signal sequence directing the synthesized product into the pathways of secretion of the target cell. This signal sequence can be the natural signal sequence of the gene in question (therapeutic or immunoprotective) where appropriate, but it can also be any other functional signal sequence or an artificial signal sequence.

As mentioned above, different configurations may be envisaged for the production of the vectors of the invention. The vectors of the invention can, in the first place, contain the two genes in the form of a single transcriptional entity. In this configuration, the two recombinant DNAs are adjacent, arranged in such a way that both genes are under the control of a single promoter and give rise to a single premessenger RNA. This configuration is advantageous since it enables a single transcription promoter to be used to regulate the expression of both genes. Moreover, this single transcriptional entity may be incorporated in the adenoviral vector in both possible orientations.

Advantageously, both recombinant DNAs contain their own transcription promoter. This configuration enables higher levels of expression to be obtained, and affords better control of the expression of the genes. In this case, the two recombinant DNAs may be inserted in the same orientation or in opposite orientations, in the same site of the adenovirus genome or at different sites.

Preferably, the recombinant DNAs are inserted at least partially in the E1, E3 or E4 regions of the adenovirus genome. When they are inserted at two different sites, it is preferable in the context of the invention to use the E1 and E3 or E1 and E4 regions. The examples show, in effect, that this organization permits a high expression of both genes without interference between the two. Advantageously, the recombinant DNAs are inserted as a replacement for viral sequences.

An especially preferred embodiment of the present invention consists of a defective adenovirus containing a first recombinant DNA containing a therapeutic gene and a second recombinant DNA containing an immunoprotective gene, in which the two recombinant DNAs are inserted in the E1 region.

An especially preferred embodiment of the present invention consists of a defective adenovirus containing a first recombinant DNA containing a therapeutic gene inserted in the E1 region, and a second recombinant DNA containing an immunoprotective gene inserted in the E3 region.

As mentioned above, the adenoviruses of the present invention are defective, that is to say they are incapable of replicating autonomously in the target cell. Generally, the genome of the defective adenoviruses according to the present invention hence lacks at least the sequences needed for replication of the said virus in the infected cell. These regions may be either removed (wholly or partially), or rendered non-functional, or replaced by other sequences, and in particular by the therapeutic genes. The defective character of the adenoviruses of the invention is an important feature, since it ensures the non-dissemination of the vectors of the invention after administration.

In a preferred embodiment, the adenoviruses of the invention comprise the ITR sequences and a sequence permitting encapsidation, and possess a deletion of all or part of the E1 gene.

The inverted repeat sequences (ITR) constitute the origin of replication of the adenoviruses. They are localized at the 3' and 5' ends of the viral genome (see FIG. 1), from where they may be isolated readily according to the traditional techniques of molecular biology known to a person skilled in the art. The nucleotide sequence of the ITR sequences of human adenoviruses (especially of the serotypes Ad2 and Ad5) is described in the literature, as well as those of canine adenoviruses (in particular CAV1 and CAV2). As regards the Ad5 adenovirus for example, the left-hand ITR sequence corresponds to the region comprising nucleotides 1 to 103 of the genome.

The encapsidation sequence (also designated Psi sequence) is needed for encapsidation of the viral DNA. This region must hence be present in order to permit the preparation of defective recombinant adenoviruses according to the invention. The encapsidation sequence is localized in the genome of the adenoviruses, between the left-hand (5') ITR and the E1 gene (see FIG. 1). It may be isolated or synthesized artificially by traditional techniques of molecular biology. The nucleotide sequence of the encapsidation sequence of human adenoviruses (especially of the serotypes Ad2 and Ad5) is described in the literature, as well as those of canine adenoviruses (in particular CAV1 and CAV2). As regards the Ad5 adenovirus for example, the encapsidation sequence corresponds to the region comprising nucleotides 194 to 358 of the genome.

More preferably, the adenoviruses of the invention comprise the ITR sequences and a sequence permitting encapsidation, and possess a deletion of all or part of the E1 and E4 genes.

In an especially preferred embodiment, the genome of the adenoviruses according to the invention carries a deletion of all or part of the E1, E3 and E4 genes, and still more preferably of all or part of the E1, E3, L5 and E4 genes.

The adenoviruses of the invention may be prepared from adenoviruses of diverse origins. There are, in effect, different serotypes of adenovirus, the structure and properties of which vary somewhat but which display a comparable genetic organization. Thus, the teachings described in the present application may be readily reproduced by a person skilled in the art for any type of adenovirus.

More especially, the adenoviruses of the invention may be of human, animal or mixed (human and animal) origin.

As regards adenoviruses of human origin, it is preferable to use those classified in group C. More preferably, among the different serotypes of human adenovirus, it is preferable to use adenoviruses type 2 or 5 (Ad2 or Ad5) in the context of the present invention.

As mentioned above, the adenoviruses of the invention may also be of animal origin, or may contain sequences originating from adenoviruses of animal origin. The Applicant has, in effect, shown that adenoviruses of animal origin are capable of infecting human cells with great efficacy, and that they are incapable of propagating in the human cells in which they have been tested (see Application FR 93/05954). The Applicant has also shown that adenoviruses of animal origin are in no way trans-complemented by adenoviruses of human origin, thereby eliminating any risk of recombination and propagation in vivo in the presence of a human adenovirus, which can lead to the formation of an infectious particle. The use of adenoviruses or of regions of adenoviruses of animal origin is hence especially advantageous, since the risks inherent in the use of viruses as vectors in gene therapy are even lower.

The adenoviruses of animal origin which may be used in the context of the present invention can be of canine, bovine, murine (for example: Mav1, Beard et al., Virology 75 (1990) 81), ovine, porcine, avian or alternatively simian (for example: SAV) origin. More especially, among avian adenoviruses, there may be mentioned the serotypes 1 to 10 which are available in the ATCC, such as, for example, the strains Phelps (ATCC VR-432), Fontes (ATCC VR-280), P7-A (ATCC VR-827), IBH-2A (ATCC VR-828), J2-A (ATCC VR-829), T8-A (ATCC VR-830), K-11 (ATCC VR-921) or alternatively the strains referenced ATCC VR-831 to 835. Among bovine adenoviruses, the different known serotypes may be used, and in particular those available in the ATCC (types 1 to 8) under the references ATCC VR-313, 314, 639-642, 768 and 769. There may also be mentioned murine adenoviruses FL (ATCC VR-550) and E20308 (ATCC VR-528), ovine adenovirus type 5 (ATCC VR-1343) or type 6 (ATCC VR-1340), porcine adenovirus 5359), or simian adenoviruses such as, in particular, the adenoviruses referenced in the ATCC under the numbers VR-591–594, 941–943, 195–203, and the like.

Among the different adenoviruses of animal origin, it is preferable in the context of the present invention to use adenoviruses or regions of adenoviruses of canine origin, and in particular all strains of CAV2 adenoviruses [strain Manhattan or A26/62 (ATCC VR-800) for example]. Canine adenoviruses have been subjected to many structural studies. Thus, complete restriction maps of CAV1 and CAV2 adenoviruses have been described in the prior art (Spibey et al., J. Gen. Virol. 70 (1989) 165), and the E1a and E3 genes as well as the ITR sequences have been cloned and sequenced (see, in particular, Spibey et al., Virus Res. 14 (1989) 241; Linne, Virus Res. 23 (1992) 119, WO 91/11525).

The defective recombinant adenoviruses according to the invention may be prepared in different ways.

A first method consists in transfecting the DNA of the defective recombinant virus prepared in vitro (either by ligation or in plasmid form) into a competent cell line, that is to say one carrying in trans all the functions needed for complementation of the defective virus. These functions are preferably integrated in the genome of the cell, thereby enabling risks of recombination to be avoided and endowing the cell line with enhanced stability.

A second approach consists in cotransfecting the DNA of the defective recombinant virus prepared in vitro (either by ligation or in plasmid form) and the DNA of a helper virus into a suitable cell line. According to this method, it is not necessary to have at one's disposal a competent cell line capable of complementing all the defective functions of the recombinant adenovirus. A part of these functions is, in effect, complemented by the helper virus. This helper virus must itself be defective, and the cell line carries in trans the functions needed for its complementation. Among cell lines which may be used, in particular, in the context of this second approach, the human embryonic kidney line 293, KB cells, Hela, MDCK, GHK cells, and the like, may be mentioned in particular (see examples).

Thereafter, the vectors which have multiplied are recovered, purified and amplified according to traditional techniques of molecular biology.

According to a variant of embodiment, it is possible to prepare in vitro, either by ligation or in plasmid form, the DNA of the defective recombinant virus carrying the appropriate deletions and the two recombinant DNAs. As mentioned above, the vectors of the invention advantageously possess a deletion of all or part of certain viral genes, in particular the E1, E3, E4 and/or L5 genes. This deletion may correspond to any type of elimination affecting the gene in question. It may correspond, in particular, to the elimination of all or part of the coding region of the said gene, and/or of all or part of the region promoting transcription of the said gene. The elimination is generally carried out on DNA of the defective recombinant virus, for example by digestion by means of suitable restriction enzymes, followed by ligation, according to the techniques of molecular biology, as illustrated in the examples. The recombinant DNAs may then be inserted into this DNA by enzymatic cleavage, followed by ligation in selected regions and in the chosen orientation.

The DNA thereby obtained, which hence carries the appropriate deletions and both recombinant DNAs, enables the defective recombinant adenovirus carrying the said deletions and recombinant DNAs to be generated directly. This first variant is particularly suited to the production of recombinant adenoviruses in which the genes are arranged in the form of a single transcriptional unit, or under the control of separate promoters but inserted at the same site of the genome.

It is also possible to prepare the recombinant virus in two steps, permitting the successive introduction of the two recombinant DNAs. Thus, the DNA of a first recombinant virus carrying the appropriate deletions (or a part of the said deletions) and one of the recombinant DNAs is constructed by ligation or in plasmid form. This DNA is then used to generate a first recombinant virus carrying the said deletions and a recombinant DNA. The DNA of this first virus is then isolated and cotransfected with a second plasmid or the DNA of a second defective recombinant virus carrying the second recombinant DNA, the appropriate deletions (portion not present on the first virus) and a region permitting homologous recombination. This second step thus generates the defective recombinant virus carrying the two recombinant DNAs. This variant of preparation is especially suitable for the preparation of recombinant viruses carrying two recombinant DNAs inserted at two different regions of the adenovirus genome.

The present invention also relates to any pharmaceutical composition comprising one or more defective adenoviruses as described above. The pharmaceutical compositions of the invention may be formulated with a view to topical, oral, parenteral, intranasal, intravenous, intramuscular, subcutaneous, intraocular, transdermal, and the like, administration.

Preferably, the pharmaceutical composition contains vehicles which are pharmaceutically acceptable for an injectable formulation. These can be, in particular, sterile, isotonic saline solutions (monosodium or disodium phosphate, sodium, potassium, calcium or magnesium chloride, and the like, or mixtures of such salts), or dry, in particular lyophilized, compositions which, on adding sterilized water or physiological saline, as the case may be, enable injectable solutions to be formed.

The doses of virus used for the injection may be adapted in accordance with different parameters, and in particular in accordance with the mode of administration used, the pathology in question, the gene to be expressed or the desired period of treatment. Generally speaking, the recombinant adenoviruses according to the invention are formulated and administered in the form of doses of between $10^4$ and $10^{14}$ pfu/ml, and preferably $10^6$ to $10^{10}$ pfu/ml. The term pfu (plaque forming unit) corresponds to the infectious power of a solution of virus, and is determined by infecting a suitable cell culture and measuring, generally after 5 days, the number of plaques of infected cells. The techniques of determination of the pfu titre of a viral solution are well documented in the literature.

The adenoviruses of the invention may be used for the treatment or prevention of a large number of pathologies. Depending on the therapeutic gene inserted, the adenoviruses of the invention may be used, in particular, for the treatment or prevention of genetic diseases (dystrophy, cystic fibrosis, and the like), neurodegenerative diseases (Alzheimer's, Parkinson's, ALS, and the like), hyperproliferative pathologies (cancers, restenosis, and the like), pathologies associated with disorders of coagulation or with dyslipoproteinaemias, pathologies associated with viral infections (hepatitis, AIDS, and the like), and the like.

The present invention will be described more completely by means of the examples which follow, which should be considered to be illustrative and nonlimiting.

LEGENDS TO THE FIGURES

FIG. 1: Genetic organization of the Ad5 adenovirus. The complete sequence of Ad5 is available on a database, and enables a person skilled in the art to select or create any restriction site, and thus to isolate any region of the genome.

GENERAL TECHNIQUES OF MOLECULAR BIOLOGY

The methods traditionally used in molecular biology, such as preparative extractions of plasmid DNA, centrifugation of plasmid DNA in a caesium chloride gradient, agarose or acrylamide gel electrophoresis, purification of DNA fragments by electroelution, phenol or phenol-chloroform extraction of proteins, ethanol or isopropanol precipitation of DNA in a saline medium, transformation in *Escherichia coli*, and the like, are well known to a person skilled in the art and are amply described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

Plasmids of the pBR322 and pUC type and phages of the M13 series are of commercial origin (Bethesda Research Laboratories).

To carry out ligation, the DNA fragments may be separated according to their size by agarose or acrylamide gel electrophoresis, extracted with phenol or with a phenol-chloroform mixture, precipitated with ethanol and then incubated in the presence of phage T4 DNA ligase (Biolabs) according to the supplier's recommendations.

The filling in of 5' protruding ends may be performed with the Klenow fragment of *E. coli* DNA polymerase I (Biolabs) according to the supplier's specifications. The destruction of 3' protruding ends is performed in the presence of phage T4 DNA polymerase (Biolabs) used according to the manufacturer's recommendations. The destruction of 5' protruding ends is performed by a controlled treatment with S1 nuclease.

In vivo site-directed mutagenesis using synthetic oligodeoxynucleotides may be performed according to the method developed by Taylor et al. [Nucleic Acids Res. 13 (1985) 8749–8764] using the kit distributed by Amersham.

The enzymatic amplification of DNA fragments by the so-called PCR [polymerase-catalysed chain reaction, Saiki R. K. et al., Science 230 (1985) 1350–1354; Mullis K. B. and Faloona F. A., Meth. Enzym. 155 (1987) 335–350] technique may be performed using a "DNA thermal cycler" (Perkin Elmer Cetus) according to the manufacturer's specifications.

Verification of the nucleotide sequences may be performed by the method developed by Sanger et al. [Proc. Natl. Acad. Sci. USA, 74 (1977) 5463–5467] using the kit distributed by Amersham.

Cell Lines Used

In the examples which follow, the following cell lines have or may be used:

Human embryonic kidney line 293 (Graham et al., J. Gen. Virol. 36 (1977) 59). This line contains, in particular, integrated in its genome, the left-hand portion of the Ad5 human adenovirus genome(12%).

KB human cell line: Originating from a human epidermal carcinoma, this line is available in the ATCC (ref. CCL17), together with the conditions enabling it to be cultured.

Hela human cell line: Originating from a human epithelial carcinoma, this line is available in the ATCC (ref. CCL2), together with the conditions enabling it to be cultured.

MDCK canine cell line: The conditions of culture of MDCK cells have been described, in particular, by Macatney et al., Science 44 (1988) 9.

gm DBP6 cell line (Brough et al., Virology 190 (1992) 624). This line consists of Hela cells carrying the adenovirus E2 gene under the control of the MMTV LTR.

EXAMPLES

Example 1.

Construction of defective recombinant adenoviruses comprising a therapeutic gene (the *E. coli* LacZ gene) under the control of the RSVLTR promoter and the gp19k gene under the control of the RSVLTR promoter, both inserted in the E1 region.

These adenoviruses were constructed by homologous recombination between a plasmid carrying the left-hand portion of the Ad5 adenovirus, the two recombinant DNAs and a region of the Ad5 adenovirus (corresponding to protein IX) and the DNA of a defective adenovirus carrying different deletions.

1. Construction of the Vector pAD5-gp19k-βgal (FIG. 3)
1.1. Construction of the Plasmid pGEM-gp19k Plasmid pAD5-gp19k-βgal contains a cDNA sequence coding for the adenovirus gp19k protein. This plasmid was constructed as follows. The XbaI fragment of the wild-type Ad5 adenovirus genome containing the E3 region was isolated and cloned at the corresponding site of plasmid pGEM (Promega) to generate the plasmid pGEM-3. The HinfI fragment containing the gp19k coding sequence (nucleotides 28628 to 29634 of the wild-type Ad5 adenovirus) was then isolated from plasmid pGEM-E3. The ends of this fragment were rendered blunt by the action of the Klenow fragment of *E.coli* DNA polymerase I (see General techniques of molecular biology), and the fragment obtained was then cloned at the SmaI site of plasmid pGEMzf+ (Promega).

Figure 3:
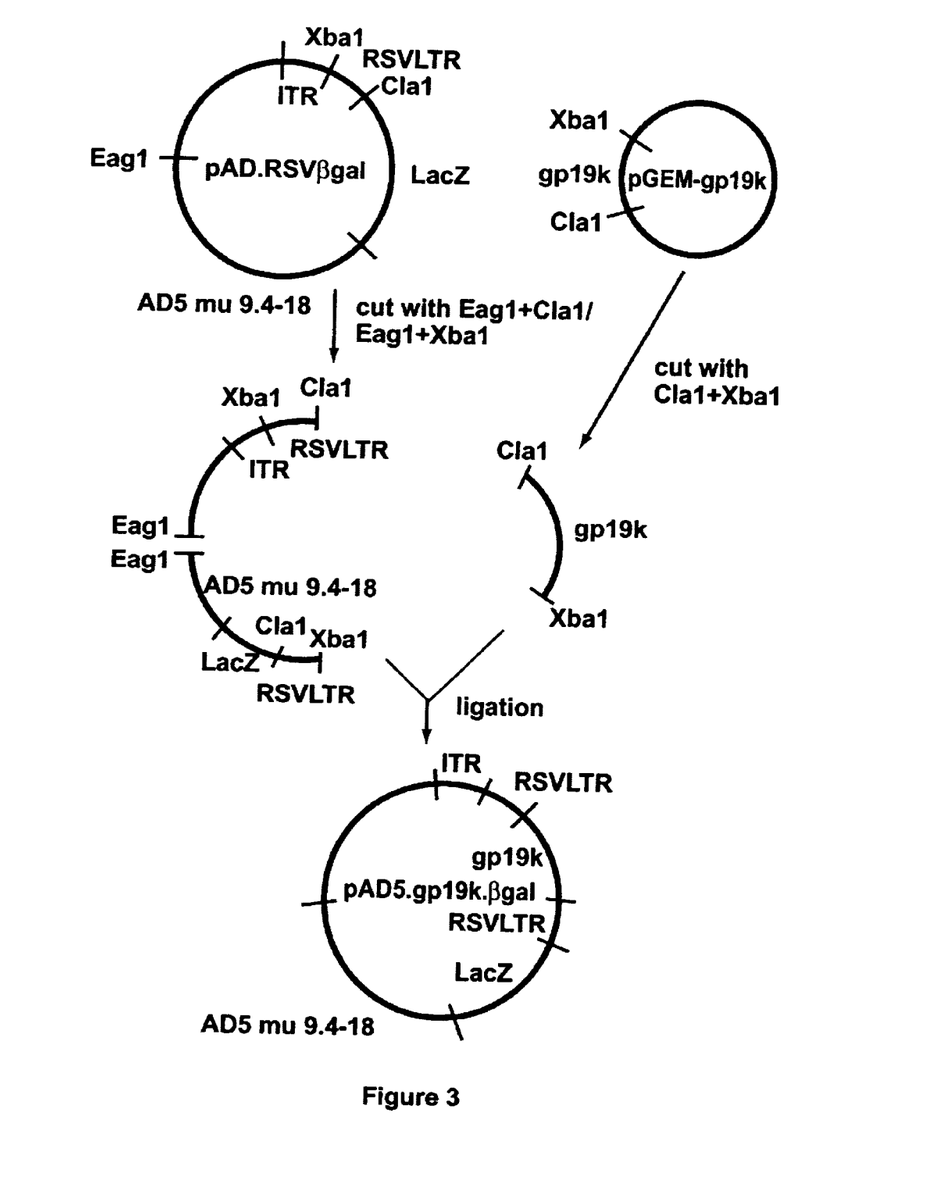
FIG. 3: Construction of the vector pAD5-gp19k-βgal.

The plasmid obtained was designated pGEM-gp19k (FIG. 3).

1.2. Construction of the Vector pAD5-gp19k-βgal

This example describes the construction of a plasmid containing one of the two recombinant DNAs comprising their own promoter, the left-hand portion of the adenovirus genome and an additional portion (protein pIX) permitting homologous recombination. This vector was constructed from the plasmid pAd.RSVβGal as follows.

Plasmid pAd.RSVβGal contains, in the 5'→3' orientation, the PvuII fragment corresponding to the left-hand end of the Ad5 adenovirus, comprising: the ITR sequence, the origin of replication, the encapsidation signals and the E1A enhancer;

the gene coding for β-galactosidase under the control of the RSV promoter (from Rous sarcoma virus), a second fragment of the Ad5 adenovirus genome, which permits homologous recombination between plasmid pAd.RSVβGal and the adenovirus dl324. Plasmid pAd.RSVβGal has been described by Stratford-Perricaudet et al. (J. Clin. Invest. 90 (1992) 626).

Plasmid pAd.RSVβGal was first cut with the enzymes EagI and ClaI. This generates a first fragment carrying, in particular, the left-hand portion of the AdS adenovirus and the RSVLTR promoter. In parallel, plasmid pAD.RSVβGal was also cut with the enzymes EagI and XbaI. This generates a second type of fragment carrying, in particular, the RSV-LTR promoter, the LacZ gene and a fragment of the Ad5 adenovirus genome which permits homologous recombination. ClaI-EagI and EagI-XbaI fragments were then ligated in the presence of the XbaI-ClaI fragment of plasmid pGEM-gp19k (Example 1.1) carrying the gp19k coding sequence (see FIG. 3). The vector thereby obtained, designated pAD5-gp19k-βgal, hence contains the PvuII fragment corresponding to the left-hand end of the AdS adenovirus comprising: the ITR sequence, the origin of replication, the encapsidation signals and the E1A enhancer;

the sequence coding for gp19k under the control of the RSV promoter (from Rous sarcoma virus);

the gene coding for β-galactosidase under the control of the RSV promoter (from Rous sarcoma virus), and a second fragment of the Ad5 adenovirus genome, which permits homologous recombination.

2. Construction of Recombinant Adenoviruses 2.1. Construction of a recombinant adenovirus carrying a deletion in the E1 region, and carrying the two recombinant DNAs inserted in the same orientation in the E1 region.

The vector pAD5-gp19k-βgal was linearized and cotransfected with an adenoviral vector deficient in the E1 gene into helper cells (line 293) supplying in trans the functions encoded by the adenovirus E1 (E1A and E1B) regions.

More specifically, the adenovirus Ad-gp19k-βgal,ΔE1 is obtained by homologous recombination in vivo between the adenovirus Ad-RSVβgal (see Stratford-Perricaudet et al. cited above) and the vector pAD5-gp19k-βgal, according to the following protocol: plasmid pAD5-gp19k-βgal, linearized with XmnI, and the adenovirus Ad-RSVβgal, linearized with the enzyme ClaI, are cotransfected into the line 293 in the presence of calcium phosphate to permit homologous recombination. The recombinant adenoviruses thereby generated are then selected by plaque purification. After isolation, the DNA of the recombinant adenovirus is amplified in the cell line 293, leading to a culture supernatant containing the unpurified defective recombinant adenovirus having a titre of approximately $10^{10}$ pfu/ml.

The viral particles are generally purified by centrifugation on a caesium chloride gradient according to known techniques (see, in particular, Graham et al., Virology 52 (1973) 456). The adenovirus Ad-gp19k-βgal,ΔE1 may be stored at −80° C. in 20% glycerol.

Figure 4:
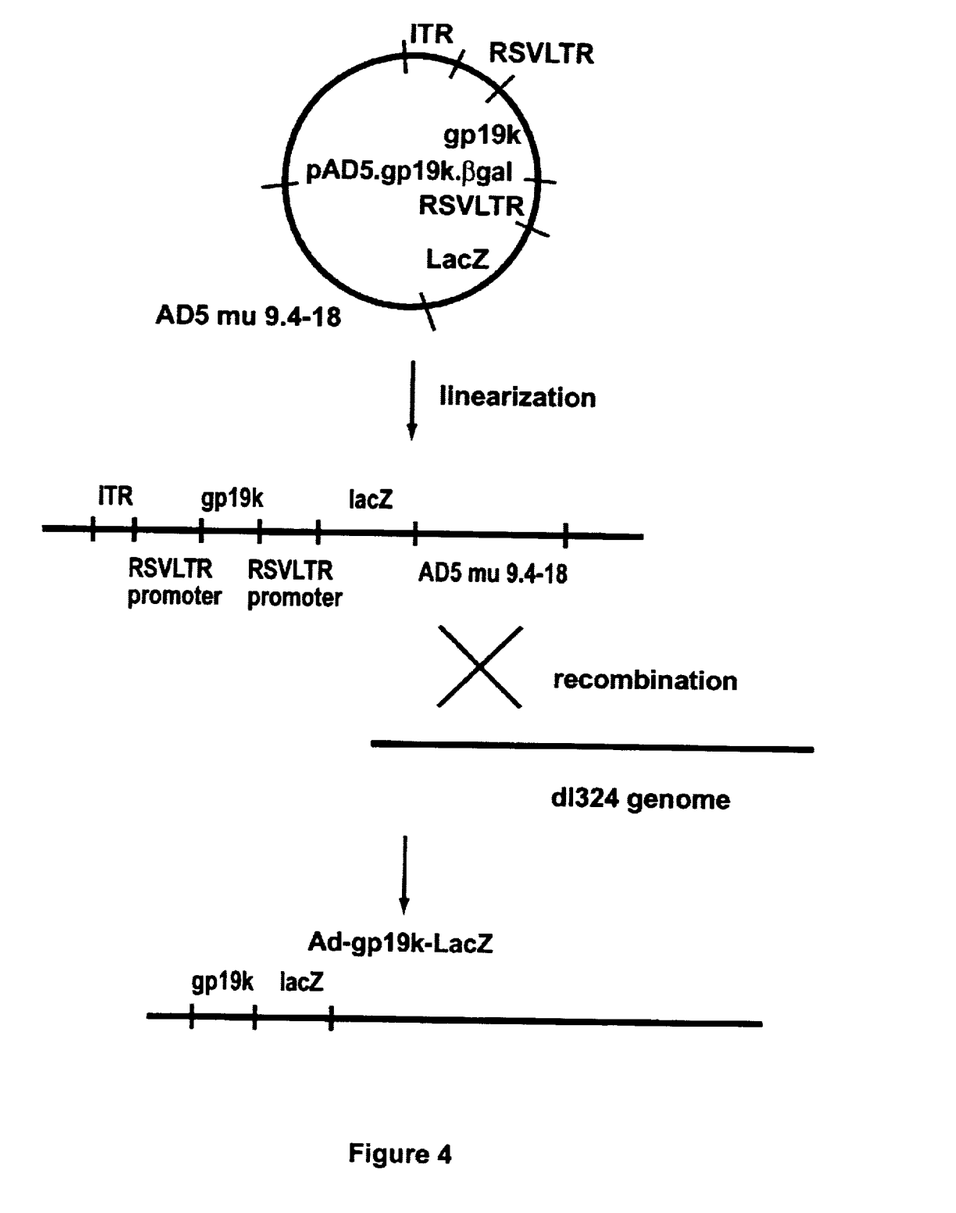
FIG. 4: Construction of the adenovirus Ad-gp19k-βgal, ΔE1,ΔE3.

2.2. Construction of a recombinant adenovirus carrying a deletion in the E1 and E3 regions, and carrying the two recombinant DNAs inserted in the same orientation in the E1 region (FIG. 4).

The vector pAD5-gp19k-βgal was linearized and cotransfected with an adenoviral vector deficient in the E1 and E3 genes into helper cells (line 293) supplying in trans the functions encoded by the adenovirus E1 (E1A and E1B) regions.

More specifically, the adenovirus Ad-gp19k-βgal,ΔE1, ΔE3 was obtained by homologous recombination in vivo between the mutant adenovirus Ad-dl1324 (Thimmappaya et al., Cell 31 (1982) 534) and the vector pAD5-gp19k-βgal, according to the following protocol: plasmid pAD5-gp19k-βgal and the adenovirus Ad-dl1324, the latter being linearized with the enzyme ClaI, were cotransfected into the line 293 in the presence of calcium phosphate to permit homologous recombination. The recombinant adenoviruses thereby generated were then selected by plaque purification. After isolation, the DNA of the recombinant adenovirus was amplified in the cell line 293, leading to a culture supernatant containing the unpurified defective recombinant adenovirus having a titre of approximately $10^{10}$ pfu/ml.

The viral particles are generally purified by centrifugation on a caesium chloride gradient according to known techniques (see, in particular, Graham et al., Virology 52 (1973) 456). The genome of the recombinant adenovirus is then verified by Southern blot analysis. The adenovirus Ad-gp19k-βgal,ΔE1,ΔE3 may be stored at −80° C. in 20% of glycerol.

Example 2

Demonstration in Cell Culture of the Functionality of the Adenoviruses of the Invention 1. Transcription of gp19k in 3T3 Fibroblasts The appearance of transcripts coding for gp19k in cells infected with the adenovirus Ad-gp19k-βgal,ΔE1,ΔE3 was demonstrated by Northern blot analysis of the total cellular RNAs. To this end, $5 \times 10^6$ 3T3 cells were infected with 40 pfu/cell of virus. After 36 hours, total cellular RNAs were recovered by means of RNAzol (Cinna/Biotecx), precipitated and then resuspended in water. 10 µg were then applied to formaldehyde gel containing 1.5% of agarose. The RNAs were then denatured in the presence of 0.05 M NaOH, and thereafter transferred onto a nylon support (Hybond+, Amersham) by capillary transfer with 20×SSC. The nylon membrane was prehybridized in medium comprising 6×SSC, 5×Denhardt's, 0.5% SDS and 100 µg of denatured salmon sperm DNA for 2 h at 60° C. A probe corresponding to the DNA of the Ad5 adenovirus E3 region, labelled with $^{32}$P using the MegaPrime kit (Amersham), was then added to the solution and left to hybridize overnight. After hybridization, the membrane was washed twice in a 2×SSC, 0.1% SDS medium at room temperature, then twice in a 0.1×SSC, 0.5% SDS medium at 45° C., then lastly in a 0.1×SSC medium at room temperature, and exposed.

The results obtained show the appearance of a 1.6-kb band in cells infected with the adenovirus Ad-gp19k-βgal, ΔE1,ΔE3. This band corresponds to an mRNA comprising the sequence coding for gp19k and extending as far as the polyA site located in the RSV promoter controlling the transcription of the LacZ gene. In contrast, no equivalent band is detected in cells infected with the adenovirus Ad-βgal.

2. Expression of a Functional gp19k

The functionality of the gp19k produced by cells infected with the adenovirus Ad-gp19k-βgal,ΔE1,ΔE3 was verified by measuring, in an ELISA test, the expression of $β_2$-microglobulin at the surface of the cells. $β_2$-Microglobulin is a nontransmembrane protein localized at the cell surface in combination with MHC-I molecules, and which is needed for presentation of the antigen at the cell surface. In particular, it is needed for correct folding of the MHC-I molecules and for the presentation of antigenic peptides at the cell surface, and constitutes as a result a good marker of the functionality of the MHC-I molecules.

3T3-Balb-c cells at confluence were infected with 200 pfu/cell of Ad-gp19k-βgal,ΔE1,ΔE3, and then incubated for 40 h at 37° C. under a humid atmosphere, 5% $CO_2$, in DMEM medium containing 10% of foetal calf serum. The cells were then harvested in PBS buffer, 20 mM EDTA, and suspended in DMEM medium, 10% FCS. $10^5$ cells were then introduced into each well of a 96-well plate. The plates were centrifuged at 250 g for 3 min and then incubated for 6 hours. The wells were then washed with PBS buffer, 1% bovine albumin (BSA) and thereafter incubated with a 1/500 dilution of sheep anti-$β_2$-microglobulin antibody (The Binding Site, Birmingham UK) in 1% BSA-PBS for 20 min at 37° C. The cells were then washed in 1% BSA-PBS, thereafter fixed in PBS buffer, 0.37% formaldehyde, 0.2% glutaraldehyde, washed twice and incubated with a 1/35,000 dilution in 1% BSA-PBS of a 2nd anti-sheep antibody conjugated to alkaline phosphatase (AP) (Sigma) for 1 hour at 4° C. The plates were then washed 3 times in 1% BSA-PBS. The AP activity was then detected using the AP substrate kit (Biorad). The optical density of the wells being read at 450 nm, the mean OD and the standard deviation were calculated.

The results obtained show that infection with Ad-gp19k-βgal,ΔE1,ΔE3 induces an approximately 40% reduction in the intensity of the surface $β_2$-microglobulin signal revealed by the ELISA test, relative to the effect produced by the adenovirus Ad-βgal. These results show clearly that Ad-gp19k-βgal,ΔE1,ΔE3 induces the production of a functional gp19k protein, and that the latter induces a significant fall in the expression of MHC-I molecules at the cell surface.

Example 3

Immunoprotective Effect of the Adenoviruses of the Invention 3.1. Sensitivity to CTL Stimulated in Vivo with the Adenovirus Ad-βgal This example shows that cells infected with the adenovirus Ad-gp19k-βgal,ΔE1,ΔE3 are protected from lysis by CTL relative to cells infected with an Ad-βgal adenovirus.

DBA/2 mice (H-2d) received a first intravenous injection of $10^8$ pfu of virus Ad-βgal, followed 3 weeks later by a further intrapetitoneal injection of the same amount of virus. The mice were sacrificed 2 weeks later (at the earliest), their spleen was ground and the spleen cells were suspended in 10 ml of RPMI 1640 (Gibco) containing 10% of decomplemented FCS, 50 µg/ml of streptomycin, 100 U/ml of penicillin, 100 µg/ml of kanamycin and 100 µg/ml of gentamicin. The cells thereby obtained (CTL lymphocytes) were then incubated in the presence of 3T3 cells infected with the adenovirus Ad-βgal. This leads to a lysis of approximately 40% of the stained (i.e. infected) cells. In contrast, these same cells (CTL lymphocytes) have practically no effect on uninfected fibroblasts, or on fibroblasts infected with the adenovirus Ad-gp19k-βgal,ΔE1,ΔE3. These results show clearly that incorporation in the vectors of the invention of a recombinant DNA capable of producing gp19k induces an immunoprotection of the infected cells.

3.2. Sensitivity to CTL Stimulated in Vivo with the Adenovirus Ad-gp19k-βgal,ΔE1,ΔE3

This example shows that cells infected with the adenovirus Ad-gp19k-βgal,ΔE1,ΔE3 are protected from lysis by CTL relative to cells infected with an Ad-βgal adenovirus.

Spleen cells of mice which had received injections of Ad-gp19k-βgal,ΔE1,ΔE3 were prepared under the conditions described above. Under the conditions described above, these CTL stimulated in the presence of 3T3 cells infected with Ad-gp19k-βgal,ΔE1,ΔE3 do not induce lysis of the said cells, or of uninfected fibroblasts, or of fibroblasts infected with Ad-βgal. Moreover, it was verified that this absence of lysis was not due to a poor viability of the cells. To this end, the same lymphocytes were then stimulated in the presence of 3T3 cells infected with Ad-βgal, with the object of amplifying all the anti-βgal or antiadenovirus clones. The lymphocytes thereby obtained are capable of lysing 3T3 cells infected with Ad-βgal, in the same manner as those removed from mice which had received Ad-βgal. These results show clearly (i) that the vectors of the invention induce an immunoprotection of the infected cells, since no effective specific CTL is generated, and (ii) that while some anti-vector lymphocytes are generated in the spleens of mice injected with Ad-gp19k-βgal,ΔE1,ΔE3, the expression of the antigens during ex vivo stimulation is insufficient to induce a clonal expansion of these lymphocytes which is necessary for the lysis of the infected target cells.

Example 4

Construction of defective recombinant adenoviruses comprising a therapeutic gene under the control of a promoter inserted in the E1 region, and the gp19k gene under the control of the RSVLTR promoter inserted in the E3 region.

These adenoviruses were constructed by homologous recombination between a the DNA of a first defective virus carrying the first recombinant DNA (therapeutic gene+ promoter) inserted in the E1 region, and the DNA of a second defective adenovirus carrying the second recombinant DNA (gp19k+RSV promoter) inserted in the E3 region.

1. Construction of the Defective Virus Carrying the Second Recombinant DNA (gp19k+RSV Promoter) Inserted in the E3 Region This virus was constructed from the adenovirus Add1324 (Thimmappaya et al., Cell 31 (1982) 543). This virus carries a deletion in the E1 region and in the E3 region (XbaI-EcoRI fragment deleted). The Add1324 virus DNA was isolated and purified. This DNA was then cut with the enzymes XbaI and EcoRI. An XbaI-EcoRI fragment was then obtained from plasmid pAd-gp19k-βgal carrying the sequence coding for gp19k under the control of the RSV promoter, and thereafter inserted in the said sites into the Add1324 DNA opened as before.

The DNA thereby obtained hence contains a deletion in the E1 region and a recombinant DNA in the E3 region carrying the gp19k gene under the control of RSV.

2. Construction of Adenoviruses Carrying Both Recombinant DNAs

The DNA of the recombinant virus prepared above and the DNA of a recombinant adenovirus carrying a therapeutic gene in the E1 region, the latter DNA being linearized with BamHI, are cotransfected into the line 293 in the presence of calcium phosphate to permit homologous recombination. The recombinant adenoviruses thereby generated are then selected by plaque purification. After isolation, the DNA of the recombinant adenovirus is amplified in the cell line 293, leading to a culture supernatant containing the unpurified defective recombinant adenovirus having a titre of approximately $10^{10}$ pfu/ml.

The viral particles are generally purified by centrifugation on a caesium chloride gradient according to known techniques (see, in particular, Graham et al., Virology 52 (1973) 456).

Although the examples above describe more especially the filled of the gp19k gene, it is to be understood that the approaches described in the examples above may be repeated by a person skilled in the art using other therapeutic genes, other immunoprotective genes, other promoters and other insertion sites in the adenovirus genome.

What is claimed is:

1. A replication defective adenoviral vector comprising a first and second recombinant DNA sequence inserted into an adenoviral genome having a deleted or non-functional E3 region, wherein the first recombinant DNA sequence can be expressed from the vector and wherein the second recombinant DNA sequence comprises the adenoviral immunoprotective E3 gp19k coding region linked to a non-adenoviral promoter, and wherein the adenoviral vector is capable of prolonged expression of the first and second recombinant DNA sequences compared to a control adenovirus.

2. The replication defective adenoviral vector according to claim 1, wherein said first and second recombinant DNA sequences are inserted into the adenovirus genome in the same orientation.

3. The replication defective adenoviral vector according to claim 1, wherein said first and second recombinant DNA sequences are inserted into the adenovirus genome in opposite orientations.

4. The replication defective adenoviral vector according to claim 1, wherein said recombinant DNA sequences are inserted into the same region of the adenovirus genome.

5. The replication defective adenoviral vector according to claim 1, wherein the first and second recombinant DNA sequences are inserted into the adenovirus genome in the E1, E3 or E4 region.

6. The replication defective adenoviral vector according to claim 1, wherein the first and second recombinant DNA sequences are inserted into the adenovirus genome in the E1 region.

7. The replication defective adenoviral vector according to claim 1, wherein the first and second recombinant DNA sequences are inserted at different sites of the adenovirus genome and wherein the sites are selected from the group consisting of the adenovirus E1, E3, L5 and E4 regions.

8. The replication defective adenoviral vector according to claim 1, wherein one recombinant DNA sequence is inserted into the adenovirus genome in the E1 region and the other recombinant DNA sequence is inserted into the adenovirus genome in the E3 or E4 region.

9. The replication defective adenoviral vector according to claim 1, wherein the first recombinant DNA sequence is operably linked to a eukaryotic or viral promoter.

10. The replication defective adenoviral vector according to claim 1, wherein the second recombinant DNA sequence comprises a constitutive promoter.

11. The replication defective adenoviral vector according to claim 1, wherein the non-adenoviral promoter is a Rous sarcoma virus LTR promoter.

12. The replication defective adenoviral vector according to claim 1, wherein the second recombinant DNA is cDNA.

13. The replication defective adenoviral vector according to claim 1, wherein the first and second recombinant DNA sequences constitute a single transcriptional entity.

14. The replication defective adenoviral vector according to claim 1, wherein the non-adenoviral promoter is selected from the group consisting of an MLP promoter, a CMV promoter, an RSV promoter, a PKG promoter, an albumin gene promoter, and a cytokine-induced promoter.

15. A replication defective adenoviral vector comprising a first and second recombinant DNA sequence inserted into an adenoviral genome having a deleted or non-functional E3 region, wherein the first recombinant DNA sequence can be expressed from the vector and wherein the second recombinant DNA sequence comprises the herpes simplex virus ICP47 coding region linked to a non-adenoviral promoter, and wherein the adenoviral vector is capable of prolonged expression of the first and second recombinant DNA sequences compared to a control adenovirus.

16. The replication defective adenoviral vector according to claim 15, wherein said first and second recombinant DNA sequences are inserted into the adenovirus genome in the same orientation.

17. The replication defective adenoviral vector according to claim 15, wherein said first and second recombinant DNA sequences are inserted into the adenovirus genome in opposite orientations.

18. The replication defective adenoviral vector according to claim 15, wherein said recombinant DNA sequences are inserted into the same region of the adenovirus genome.

19. The replication defective adenoviral vector according to claim 15, wherein the first and second recombinant DNA sequences are inserted into the adenovirus genome in the E1, E3 or E4 region.

20. The replication defective adenoviral vector according to claim 15, wherein the first and second recombinant DNA sequences are inserted into the adenovirus genome in the E1 region.

21. The replication defective adenoviral vector according to claim 15, wherein the first and second recombinant DNA sequences are inserted at different sites of the adenovirus genome and wherein the sites are selected from the group consisting of the adenovirus E1, E3, L5 and E4 regions.

22. The replication defective adenoviral vector according to claim 15, wherein one recombinant DNA sequence is inserted into the adenovirus genome in the E1 region and the other recombinant DNA sequence is inserted into the adenovirus genome in the E3 or E4 region.

23. The replication defective adenoviral vector according to claim 15, wherein the first recombinant DNA sequence is operably linked to a eukaryotic or viral promoter.

24. The replication defective adenoviral vector according to claim 15, wherein the second recombinant DNA sequence comprises a constitutive promoter.

25. The replication defective adenoviral vector according to claim 15, wherein the non-adenoviral promoter is a Rous sarcoma virus LTR promoter.

26. The replication defective adenoviral vector according to claim 15, wherein the second recombinant DNA is cDNA.

27. The replication defective adenoviral vector according to claim 15, wherein the first and second recombinant DNA sequences constitute a single transcriptional entity.

28. The replication defective adenoviral vector according to claim 15, wherein the non-adenoviral promoter is selected from the group consisting of an MLP promoter, a CMV promoter, an RSV promoter, a PKG promoter, an albumin gene promoter, and a cytokine-induced promoter.

* * * * *

UNITED STATES PATENT AND TRADEMARK OFFICE
CERTIFICATE OF CORRECTION

PATENT NO. : 6,669,942 B2
DATED : December 30, 2003
INVENTOR(S) : Michel Perricaudet et al.

It is certified that error appears in the above-identified patent and that said Letters Patent is hereby corrected as shown below:

Title page,
Item [54], "DEFECTIVE ADENOVIRUSES INCLUDING A THERAPEUTIC GENE AND AN IMMUNOPROTECTOVE GENE" should read -- ADENOVIRAL VECTORS CONTAINING AN IMMUNOPROTECTIVE GENE --

Signed and Sealed this

Thirtieth Day of March, 2004

JON W. DUDAS
*Acting Director of the United States Patent and Trademark Office*